United States Patent
Tomita et al.

[11] 3,976,789
[45] Aug. 24, 1976

[54] COSMETIC COMPOSITION

[75] Inventors: Kenichi Tomita, Yokohama; Mitsuo Yanagi, Sagamihara; Toshiaki Kobayashi, Yokohama, all of Japan

[73] Assignee: Shiseido Co., Ltd., Tokyo, Japan

[22] Filed: Feb. 1, 1974

[21] Appl. No.: 438,525

[52] U.S. Cl. ............................................. 424/365
[51] Int. Cl.² ......................................... A61K 47/00
[58] Field of Search .......................... 424/365, 64

[56] References Cited
UNITED STATES PATENTS

| | | | |
|---|---|---|---|
| 3,102,128 | 8/1963 | Hennig et al. | 424/365 |
| 3,651,102 | 3/1972 | Coopersmith | 424/365 |
| 3,826,845 | 7/1974 | Suyama et al. | 424/365 |

*Primary Examiner*—Frederick E. Waddell

[57] ABSTRACT

A cosmetic composition comprising at least one compound selected from the group consisting of saturated triesters and tetraesters having a side chain at the 2-position and having the general formula $$R(OCOR')_n$$

wherein R is an alkyl group of trimethylolethane, trimethylolpropane or pentaerythritol, R' is an alkyl group of 2-ethylhexanoic acid, 2-hexyl-decanoic acid or 2-hepty-undecanoic acid, and n is an integer of 3 and 4.

4 Claims, No Drawings

COSMETIC COMPOSITION

FIELD OF THE INVENTION

This invention relates to cosmetic composition which include at least one triester and/or tetraester of a synthetic higher fatty acid having a side chain at the 2-position thereof.

BACKGROUND OF THE INVENTION

In general, in formulating cosmetics which are directly applied to a human skin for supplying moisture, oil and the like in a hygienic manner, it is necessary to conduct strict and scientific study and examination of the constituent to be used and the processing techniques to be employed.

The surface of human skin is protected by sebum secreted from sebaceous glands. The sebum not only contributes to protect the skin from external physical and chemical stimulations, maintaining the skin in a physiologically normal state irrespective of environmental conditions, but also plays an important role in preventing invasion of harmful microorganisms. Therefore it has been a matter of great concern for cosmetic chemists to find materials which have behaviors similar to those of the sebum as cosmetic constituent.

Each raw material for a safe cosmetic having excellent properties should meet the following requirements:

It should be non-irritant.

It should by physically stable, that is, it should not solidify even at low temperatures.

It should exhibit no biodegradability. In other words, it should be free from the contamination of germs.

It should be chemically stable without undergoing hydrolysis.

It should have low oral and percutaneous toxicity.

SUMMARY OF THE INVENTION

It is an object of the present invention to provide a cosmetic having a composition which meets the above-mentioned requirements.

It is another object of the present invention to provide a cosmetic which has physical, chemical and microbiological stability.

It is a further object of the present invention to provide a cosmetic which comprises at least one of triester and/or tetraester a higher fatty acid having a side chain at its 2-position.

DETAILED DESCRIPTION OF THE INVENTION

The cosmetic composition of the present invention comprises a compound expressed by the general formula

wherein R is an alkyl group of trimethylolethane, trimethylolpropane, or pentaerythritol, R' is an alkyl group of 2-ethylhexanoic acid, 2-hexyl-decanoic acid or 2-heptyl-undecanoic acid, and n is an integer of 3 and 4.

One of the important features of the present invention is that the compound be in the form of a triester and/or tetraester so that non-irritant properties similar to a triglyceride contained in the sebum can be attained.

Another feature of the present invention resides in that, for non-solidification at low temperatures, which is generally carried out either by an unsaturation treatment or by a saturation treatment by attaching a side chain to the compound, the compound of the present invention is saturated with a side chain at a particular position in view of its greater oxidation stability. Furthermore, resistanceibility to biodegradability and hydrolysis can be imparted by said saturation treatment, in which the side chain group is attached to the compound at a position in the vicinity of the ester group, i.e., the 2-position, so as to attain the aforementioned improved properties by steric hindrance of the side chain at the 2-position against the ester group.

Still another feature of the present invention resides in that the triester and tetraester used in this invention have no oral and percutaneous toxicity.

The triester and tetraester useful in the present invention can be prepared by using as a polyhydroxy alcohol trimethylolethane, trimethylolpropane, or pentaerythritol and as a saturated fatty acid having a side chain at the 2-position 2-ethyl-hexanoic acid, 2-hexyl-decanoic acid, or 2-heptyl-undecanoic acid. Particularly, examples of the triester and tetraester include trimethylolethane-tri-2-ethyl-hexanoate, trimethylolpropane-tri-2-ethyl-hexanoate, pentaerythritol-tetra-2-ethyl-hexanoate, trimethylolethane-tri-2-hexyl-decanoate, trimethylolpropane-tri-2-hexyl-decanoate, pentaerythritol-tetra-2-hexyl-decanoate, trimethylolethane-tri-2-heptyl-undecanoate, trimethylolpropane-tri-2-heptyl-undecanoate and pentaerythritol-tetra-2-heptyl-undecanoate.

The esters may be employed in various forms of cosmetics such as a cream, a lotion, a lipstick, a foundation, a hair dressing or a bath oil.

The preparation of the triester or tetraester is particularly illustrated in the following examples.

Synthesis Example 1

Preparation of trimethylolpropane-tri-2-ethyl-hexanoate:

0.87 mols of trimethylolpropane were mixed with 3.47 mols of 2-ethyl-hexanoic acid with sufficient stirring. Then, 0.05 mols of sulfuric acid (as a catalyst for esterification) and carbon black (as a decoloring agent) in an amount of 3 wt% of the total amount of the polyhydroxy alcohol and the acid were further added to the mixture, which was stirred at 200° – 220°C for about 3 hours while removing water from the reaction system. After completion of the reaction, the carbon black was filtered out from the reaction system. Thereafter, the resultant reaction mixture was washed with water several times for removal therefrom of the sulfuric acid catalyst. The thus washed mixture was dried over anhydrous sodium sulfate, and thereafter was subjected to simple distillation to remove any excess of 2-ethyl-hexanoic acid from the reaction mixture. Subsequently, colorless and odorless trimethylolpropane-tri-2-ethyl-hexanoate was obtained by molecular still-distillation. The yield was 87 % and the ester had a density of 0.9420 – 0.9430 (at 26°C), a viscosity of 42 – 43 centipoises (at 26°C) and, as determined by gas chromatography, a purity of greater than 99.9 %.

Synthesis Example 2

Preparation of pentaerythritol-tetra-2-ethyl-hexanoate:

0.758 mols of pentaerythritol, 3.80 mols of 2-ethyl-hexanoic acid and 0.06 mols of sulfuric acid as an ester catalyst were treated in the same manner as in Synthesis Example 1, to obtain colorless and odorless pentaerythritol-tetra-2-ethyl-hexanoate. The yield was 82 % and the ester had a density of 0.9600 – 0.9610 (at 26°C), a viscosity (at 26°C) of 81 – 82 centipoises, and, as determined by gas chromatography, a purity of 99.9 %.

Trimethylolethane-tri-2-ethyl-hexanoate, trimethylolethane-tri-2-hexyl-decanoate, trimethylolethane-tri-2-heptyl-undecanoate, trimethylolpropane-tri-2-hexyl-decanoate, pentaerythritol-tetra-2-hexyl-decanoate, trimethylolpropane-tri-2-heptyl-undecanoate and pentaerythritol-tetra-2-heptyl-undecanoate were also prepared in the same manner as in Synthesis Example 1.

Nine kinds of the esters thus prepared were then tested on animal and human skin for the assurance of safety and compared with four control substances, i.e., trimethylolethane-tri-n-caprylate, trimethylolpropane-tri-n-caprylate, pentaerythritol-tetra-n-caprylate and glycelol-tri-n-caprylate.

1. Animal Test 1-1. Primary Skin Irritation Test-Rabbits

Testing Method: Albino rabbits having a weight of 2.3–3 kg were employed. Eight albino rabbits, each with its back previously clipped, were divided into two groups, one for an intact skin procedure and the other for an abraded skin procedure. All the test rabbits were immobilized in a multiple animal restrainer.

The above-mentioned 13 kinds of testing substances were each applied in an amount of 0.5 ml on eight pieces of lint cloth each having a size of 2.5 × 2.5 cm and plastered on the backs of the eight rabbits. The applied lint cloth was secured by a gauze having a size of 3.5 × 3.5 cm and fixed thereto with adhesive plaster tapes. Then, the lint cloth-applied portions were wrapped with a dentist's moisture proof rubber sheet. After a 24-hour exposure period, the lint cloth was removed to determine the skin irritation according to the "Evaluation of Irritation" described hereinlater. Then, the skin was again covered and skin irritation was evaluated again after 72 hours. The final evaluation score was determined in terms of an average value of the scores at 24 hours and at 72 hours. (Evaluation of each testing substance was expressed by way of a sum of two average values obtained by the intact skin procedure and the abraded skin one.)

Evaluation of Irritation:

1. Erythema and Eschar: red coloration
     0 = None.
     1 = Slight redness visible but not well defined.
     2 = Moderate, redness is well defined.
     3 = Severe, crimson red.
     4 = Severe erythema with slight eschar
  2. Edema: accumulation of fluid within tissue
     0 = None.
     1 = Very Slight.
     2 = Slight.
     3 = Moderate (having a size of about 1 mm)
     4 = Severe (having a size of greater than 1 mm and expanding beyond exposed area)

| Evaluation on Tested Substance: | (Sum of Two Average Values for Evaluation of Irritation) |
|---|---|
| Average Value | Evaluation |
| Less than 2 | No or almost no irritation |
| 2.1 – 3.0 | Moderate irritation |
| Greater than 3.0 | Intensive irritation |

The test results are shown in Table 1 wherein a numerical value indicates a sum of the two average values calculated on the basis of evaluation standards for the intact skin procedure and the abraded skin procedure.

2. Test on Human Skin

The test was carried out after the assurance of safety by animal test.

2-1. Primary Skin Irritation Test - Human

Closed patch test (as provided in the Schwarztweck Method):

Testing Method: The substances to be tested were applied to upper arms or brachium bending portions. The substances were each applied on a lint cloth having a diameter of 1.5 cm, which was then applied to the testing area. The thus applied cloth was covered with adhesive plaster, which was further covered by a bandage. Up to six testing cloth pieces were applied to one person.

Reaction Determination Time: readings were taken 24 hours and 48 hours after the application of the plastered cloth piece or pieces. However, where the applied substance or substances showed severe irritation on the tested human skin, the test was suspended.

Tested Subject: 100 healthy female volunteers.

Test Results: (−) No Reaction, (±) Slight Erythema, (+) Erythema, (++) Erythema, Edema and Papula, (+++) Erythema, Edema and Bulla The test results are shown in Table 1 below wherein a numerical value represents the number of persons per 100 volunteers, who proved positive (±, +, ++, and +++).

Table 1

| Substance Tested | Animal Test (Albino Rabbit) | Patch Test (One Hundred Females) |
|---|---|---|
| Control Substance | | |
| Glycerol-tri-n-caprylate | 0.21 | 0/100 |
| Trimethylolethane-tri-n-caprylate | 0.13 | 0/100 |
| Trimethylolpropane-tri-n-caprylate | 0.21 | 0/100 |
| Pentaerythritol-tetra-n-caprylate | 0.06 | 0/100 |
| Substance of the Invention | | |
| Trimethylolethane-tri-2-ethyl-hexanoate | 0.06 | 0/100 |
| Trimethylolpropane-tri-2-ethyl-hexanoate | 0.06 | 0/100 |
| Trimethylolethane-tri-2-heptyl-undecanoate | 0.00 | 0/100 |
| Pentaerythritol-tetra-2-ethyl-hexanoate | 0.00 | 0/100 |
| Trimethylolethane-tri-2-hexyl-decanoate | 0.00 | 0/100 |
| Trimethylolpropane-tri-2-hexyl-decanoate | 0.00 | 0/100 |

Table 1-continued

| | | |
|---|---|---|
| Pentaerythritol-tetra-2-hexyl-decanoate | 0.00 | 0/100 |
| Trimethylolpropane-tri-2-heptyl-undecanoate | 0.00 | 0/100 |
| Pentaerythritol-tetra-2-heptyl-undecanoate | 0.00 | 0/100 |

The above substances of the present invention were further subjected to a skin sensitization test on twenty healthy volunteers, but no sensitization was recognized.

3. Test on Biodegradability

Testing Method: Comparative substances and the substances of the present invention were each introduced into a 100 ml shouldered shaking flask, which contained 30 ml of a culture medium having the composition given herebelow, in an amount of 1 % by volume. The flask was then placed in an autoclave for sterilization of the content at 120°C for 20 min, followed by cooling. Thereafter, *Pseudomonas fluoroscens* and *Staphyloccus epidermidis* were introduced into the medium and cultured in an aerobic atmosphere at 30°C for 7 days with shaking. After 7 days, the culture solution was subjected to extraction with use of n-hexane. The resultant extract was in turn subjected to a thin layer chromatography and to gas chromatography for determination of degradability of the germs.

| Composition of Culture Medium | |
|---|---|
| Potassium Phosphate, Monobasic | 0.5 g |
| Potassium Phosphate, Dibasic | 2.5 g |
| Magnesium Sulfate | 0.3 g |
| Ammonium Sulfate | 3.0 g |
| Sodium Chloride | 0.3 g |
| Calcium Chloride (anhydride) | 0.3 g |
| Ion-exchanged Water | 1000 ml |

The biodegradability was evaluated by means of the following symbols:
++ ... Violent Degradation
+ ... Degradation
± ... Undeterminable Degradation
− ... No Degradation The test results are shown in Table II below.

Table II

| Tested Substance Germ | Pseudomonas fluorescens | Staphylococcus epidermidis |
|---|---|---|
| Control Substance | | |
| Glycerol-tri-n-caprylate | ++ | + |
| Trimethylolethane-tri-n-caprylate | ++ | ± |
| Trimethylolpropane-tri-n-caprylate | ++ | ± |
| Pentaerythritol-tetra-n-caprylate | ++ | + |
| Substance of the Invention | | |
| Trimethylolethane-tri-2-ethyl-hexanoate | − | − |
| Trimethylolethane-tri-2-hexyl-decanoate | − | − |
| Trimethylolpropane-tri-2-ethyl-hexanoate | − | − |
| Pentaerythritol-tetra-2-ethyl-hexanoate | − | − |
| Trimethylolethane-tri-2-heptyl-undecanoate | − | − |
| Trimethylolpropane-tri-2-hexyl-decanoate | − | − |
| Pentaerythritol-tetra-2-hexyl-decanoate | − | − |
| Trimethylolpropane-tri-2-heptyl-undecanoate | − | − |
| Pentaerythritol-tetra-2-heptyl-undecanoate | − | − |

As is apparent from the above test results, trimethylolethane-tri-n-caprylate, trimethylolpropane-tri-n-caprylate, pentaerythritol-tetra-n-caprylate and glycerol-tri-n-caprylate, which have saturated linear fatty acid groups, are easily degraded in comparison with the saturated branched substances of the present invention, which are thus lacking biodegradability.

4. Stability Test against Hydrolysis

Method: 2 g of a sample were introduced into a 50 ml Erlenmeyer flask equipped with a condenser. 30 cc of a 30 % sodium hydroxide aqueous solution were added to the flask for reaction with the sample at 65°C for 2 hours with stirring. After completion of the reaction, the reaction mixture was subjected to extraction by n-hexane and ether, followed by washing with water 3 to 4 times. The thus washed extract was dried over anhydrous sodium sulfate and the degree of hydrolysis of the sample was determined by gas chromatography.

The test results are shown in Table III below.

Table III

| Tested Substance | Hydrolyzing rate Residual Tri- or tetra-ester (Wt%) |
|---|---|
| Control Substance | |
| Glycerol-tri-n-caprylate | 78 % |
| Trimethylolpropane-tri-n-caprylate | 90 % |
| Pentaerythritol-tetra-n-caprylate | 76 % |
| Substance of the Present Invention | |
| Trimethylolpropane-tri-2-ethyl-hexanoate | 96 % |
| Pentaerythritol-tetra-2-ethyl-hexanoate | 94 % |
| Trimethylolpropane-tri-2-hexyl-decanoate | 98 % |
| Trimethylolpropane-tri-2-heptyl-undecanoate | 98 % |

From the foregoing, it will be apparent that the triesters or tetraesters of saturated fatty acids having a side chain at the 2-position give almost no adverse effects on animal and human skin. Furthermore, the esters are excellent in resistance to biodegradability and in physical stability as compared with known oils and waxes used as a cosmetic base material including glycerides, as a result of steric hindrance due to the formation of the long side chain in the esters at the 2-position, so that cosmetics including the esters of the invention do not loose stability when applied on human skin and exposed to the air. Additionally, the present esters possess other suitable properties for use as cosmetics, such as good lubrication and moisturing effect to the skin.

The present invention will be particularly illustrated by the following Examples, wherein the given substance is shown in wt. %.

Example 1

| O/W Type Nourishing Cream | |
|---|---|
| Formulation (1) | |
| Pentaerythritol-tetra-2-ethyl-hexanoate | 14 % |
| Cetyl alcohol | 3 |
| Vaseline | 5 |
| Lanolin | 2 |
| Formulation (2) | |
| Polyoxyethylene cetylalcohol ether | 3 |
| Trimethylolpropane-mono-stearate | 2 |
| Water (Ion-exchanged water) | 71 |
| Formulation (3) | |
| Perfume | Suitable Amount |
| Antiseptic | Suitable Amount |

The components of the above Formulation (1) were placed in a vessel and mixed with one another while agitating at 50° – 60°C for melting and homogenizing; the components of Formulation (2) were added to (2) for emulsication; then the components of Formulation (3) were added to obtain an O/W type nourishing cream.

Example 2

| W/O Type Nourishing Cream | |
|---|---|
| Formulation (1) | |
| Trimethylolpropane-tri-2-hexyl-decanoate | 25 % |
| Squalane | 15 |
| Beeswax | 10 |
| Lanolin | 10 |
| Formulation (2) | |
| Sorbitan-mono-oleate | 3 |
| Polyoxyethylene-sorbitan-mono-oleate | 1 |
| Water (Ion-exchanged water) | 36 |
| Formulation (3) | |
| Perfume | Suitable Amount |
| Antiseptic | Suitable Amount |

Formulation (1) was placed in a vessel and mixed under agitation at 50° – 60°C for melting and homogenizing; Formulation (2) was then added for emulsication and then Formulation (3) to obtain a W/O type nourishing cream.

Example 3

| Lipstick | |
|---|---|
| Formulation (1) | |
| Trimethylolpropane-tri-2-heptyl-undecanoate | 55 % |

Example 3-continued

| Lipstick | |
|---|---|
| Ceresine (solid paraffin) | 20 |
| Microcrystalline wax | 5 |
| Lanolin wax | 10 |
| Formulation (2) | |
| Lake | 10 |
| Pigment: Trimethylolpropane-tri-2-heptyl-undecanoate = 1 : 1 | |
| Perfume | Suitable Amount |

Formulation (1) was placed in a vessel and mixed at 95° – 100°C; to it was admixed Formulation (2). The resultant mixture was introduced into a lipstick mold to obtain a lipstick.

Example 4

| Bath Oil | |
|---|---|
| Formulation | |
| Trimethylolethane-tri-2-ethyl-hexanoate | 10 % |
| Trimethylolpropane-tri-2-ethyl-hexanoate | 15 |
| Squalane | 65 |
| Polyoxyethylene oleyl alcohol ether | 5 |
| Perfume | 5 |

The above components were mixed with one another while agitating at 40° – 50°C to obtain a bath oil.

What is claimed is:

1. In a non-irritating, physically stable, non-biodegradable, chemically stable cosmetic composition having low oral and percutaneous toxicity, comprising a carboxylic acid ester, the improvement which comprises employing at least one saturated triester or tetraester formed by the esterification reaction between an alcohol selected from the group consisting of trimethylolethane, trimethylolpropane and pentaerythritol and a carboxylic acid having a side chain at the 2-position selected from the group consisting of 2-ethyl-hexanoic acid, 2-hexyl decanoid acid and 2-heptyl-undecanoid acid, said saturated triesters and tetraesters being employed in amounts from about 14% to 55% by weight of the composition, as the carboxylic acid ester.

2. A cosmetic composition according to claim 1, wherein only one of said saturated triesters or tetraesters is present.

3. A cosmetic composition according to claim 1, wherein said saturated triester is selected from the group consisting of trimethylolethane-tri-2-ethyl-hexanoate, trimethylolethane-tri-2-hexyl-decanoate, trimethylolethane-tri-2-heptyl-undecanoate, trimethylolpropane-tri-2-ethyl-hexanoate, trimethylolpropane-tri-2-hexyl-decanoate, and trimethylolpropane-tri-2-heptyl-undecanoate.

4. A cosmetic composition according to claim 1, wherein said saturated tetraester is selected from the group consisting of pentaerythritol-tetra-2-ethyl-hexanoate, pentaerythritol-tetra-2-hexyl-decanoate and pentaerythritol-tetra-2-heptyl-undecanoate.

* * * * *